US012714410B2

(12) United States Patent
Itkowitz et al.

(10) Patent No.: US 12,714,410 B2
(45) Date of Patent: Aug. 25, 2026

(54) METHOD AND APPARATUS FOR MANIPULATING TISSUE

(71) Applicant: INTUITIVE SURGICAL OPERATIONS, INC., Sunnyvale, CA (US)

(72) Inventors: Brandon D. Itkowitz, San Jose, CA (US); Pushkar Hingwe, Los Altos, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 18/961,213

(22) Filed: Nov. 26, 2024

(65) Prior Publication Data

US 2025/0090156 A1 Mar. 20, 2025

Related U.S. Application Data

(63) Continuation of application No. 17/054,598, filed as application No. PCT/US2019/032213 on May 14, 2019, now Pat. No. 12,185,930.

(Continued)

(51) Int. Cl.

*A61B 17/02* (2006.01)
*A61B 34/00* (2016.01)

(Continued)

(52) U.S. Cl.

CPC .............. *A61B 17/02* (2013.01); *A61B 34/25* (2016.02); *A61B 34/35* (2016.02); *A61B 34/74* (2016.02); *A61B 34/76* (2016.02); *A61B 90/37* (2016.02); *G06F 3/011* (2013.01); *G06F 3/016* (2013.01); *G06F 3/04842* (2013.01); *G06F 3/0488* (2013.01); *G06T 7/0012* (2013.01); *G06T 7/11* (2017.01); *G06T 7/70* (2017.01); *A61B 2017/00199* (2013.01); *A61B 2017/00207* (2013.01); *A61B 2017/00216* (2013.01);

(Continued)

(58) Field of Classification Search

CPC ......... A61B 34/25; A61B 34/35; A61B 34/74; A61B 35/76; A61B 90/37

USPC .......................................................... 600/201

See application file for complete search history.

(56) References Cited

U.S. PATENT DOCUMENTS

| | | | |
|---|---|---|---|
| 6,714,841 B1 | 3/2004 | Wright et al. | |
| 11,547,285 B2 * | 1/2023 | Atarot | A61B 1/0016 |

(Continued)

FOREIGN PATENT DOCUMENTS

| | | |
|---|---|---|
| WO | WO-2016149345 A1 | 9/2016 |
| WO | WO-2018085694 A1 | 5/2018 |

OTHER PUBLICATIONS

Extended European Search Report for Application No. EP19803594.1, mailed on Jan. 5, 2022, 10 pages.

(Continued)

*Primary Examiner* — Eduardo C Robert
*Assistant Examiner* — Christina Negrellirodriguez
(74) *Attorney, Agent, or Firm* — Haynes & Boone, LLP.

(57) ABSTRACT

A method and apparatus for manipulating tissue. A tissue control point is displayed over an image of the tissue in a user interface. An input is received that moves the tissue control point within the user interface. A first instrument that is physically associated with the tissue is operated based on the received input to thereby manipulate the tissue.

20 Claims, 8 Drawing Sheets

Related U.S. Application Data

(60) Provisional application No. 62/671,945, filed on May 15, 2018.

(51) Int. Cl.

| | |
|---|---|
| ***A61B 34/35*** | (2016.01) |
| ***A61B 90/00*** | (2016.01) |
| ***G06F 3/01*** | (2006.01) |
| ***G06F 3/04842*** | (2022.01) |
| ***G06F 3/0488*** | (2022.01) |
| ***G06T 7/00*** | (2017.01) |
| ***G06T 7/11*** | (2017.01) |
| ***G06T 7/70*** | (2017.01) |
| *A61B 17/00* | (2006.01) |

(52) U.S. Cl.
CPC ..... *A61B 2034/744* (2016.02); *G06T 2200/24* (2013.01); *G06T 2207/10024* (2013.01); *G06T 2207/30004* (2013.01)

(56) References Cited

U.S. PATENT DOCUMENTS

| | | | | |
|---|---|---|---|---|
| 12,185,930 | B2 * | 1/2025 | Itkowitz | A61B 34/25 |
| 2001/0025183 | A1 | 9/2001 | Shahidi | |
| 2006/0058616 | A1 | 3/2006 | Marquart et al. | |
| 2007/0276423 | A1 | 11/2007 | Green | |
| 2009/0248036 | A1 | 10/2009 | Hoffman et al. | |
| 2013/0331644 | A1 * | 12/2013 | Pandya | A61B 34/30 600/102 |
| 2017/0000574 | A1 | 1/2017 | Itkowitz et al. | |
| 2021/0068799 | A1 | 3/2021 | Itkowitz et al. | |

OTHER PUBLICATIONS

International Preliminary Report on Patentability for Application No. PCT/US2019/032213, mailed on Nov. 26, 2020, 6 pages.
International Search Report and Written Opinion for Application No. PCT/US2019/032213, mailed on Aug. 20, 2019, 9 pages.
Office Action for Chinese Application No. CN201980045353.4, mailed Nov. 29, 2023, 14 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

METHOD AND APPARATUS FOR MANIPULATING TISSUE

CROSS-REFERENCE TO RELATED APPLICATIONS

This application is a continuation of U.S. application Ser. No. 17/054,598, filed Nov. 11, 2020, which is the U.S. national phase of International Application No. PCT/US2019/032213, filed May 14, 2019, which designated the U.S. and claims priority to and the benefit of U.S. Provisional Application No. 62/671,945, filed May 15, 2018, all of which are incorporated by reference herein in their entirety.

FIELD

The present disclosure is directed to medical procedures and methods for manipulating tissue during medical procedures. More particularly, the present disclosure is directed to systems and methods for manipulating tissue by controlling a virtual tissue control point displayed in a user interface.

BACKGROUND

Minimally invasive medical techniques are intended to reduce the amount of extraneous tissue that is damaged during diagnostic or surgical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments that provide a user with a field of view within the patient anatomy.

Some minimally invasive medical tools may be teleoperated, otherwise remotely operated, or otherwise computer-assisted. During a medical procedure, the clinician may need to manipulate tissue to retract the tissue, expose a target area, inspect a hidden region of tissue, or perform some other action. When manipulating the tissue, the clinician may need to consider a variety of parameters including the direction of motion, the magnitude of motion, operator instrument orientation, instrument collision avoidance, multi-instrument interference, and range of motion limits. Systems and methods are needed for simplifying and improving the clinician's experience during the process of manipulating tissue.

SUMMARY

The embodiments of the invention are summarized by the claims that follow the detailed description.

In one example embodiment, a method is provided for manipulating tissue. A tissue control point is displayed over an image of the tissue in a user interface. An input is received that moves the tissue control point within the user interface. A first instrument physically associated with the tissue is operated based on the received input to thereby manipulate the tissue.

In another example embodiment, another method is provided for manipulating tissue. A virtual object representing a tissue control point is displayed collocated with the tissue over an image of the tissue in a user interface. The virtual object is offset from a position of a first instrument. A second instrument is operated to move a proxy geometry representing the second instrument into contact with the virtual object and impart a force on the virtual object. The first instrument is operated based on the force applied to the virtual object to thereby manipulate the tissue. A haptic feedback response is generated at the second instrument in response to operation of the first instrument.

In yet another example embodiment, an apparatus comprises a display system and a control system. The display system displays an image of tissue in a user interface. The control system is communicatively coupled to the display system. The control system is configured to display a tissue control point over the image; receive an input that moves the tissue control point within the user interface; and operate an instrument physically associated with the tissue based on the received input to thereby manipulate the tissue.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
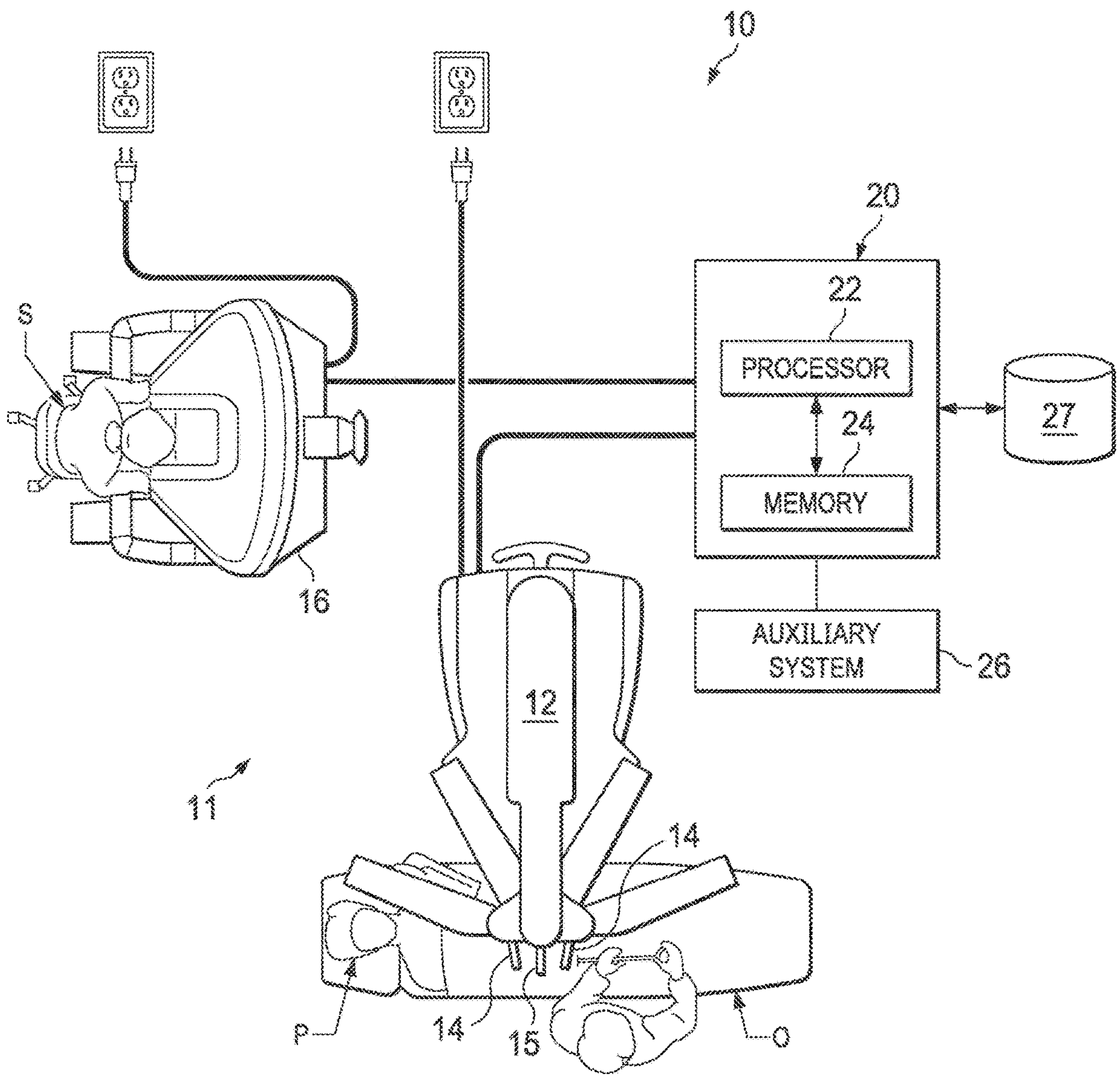
FIG. 1A is a schematic view of a medical system, in accordance with an embodiment.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, as would be appreciated by one skilled in the art, embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment may be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Figure 1B:
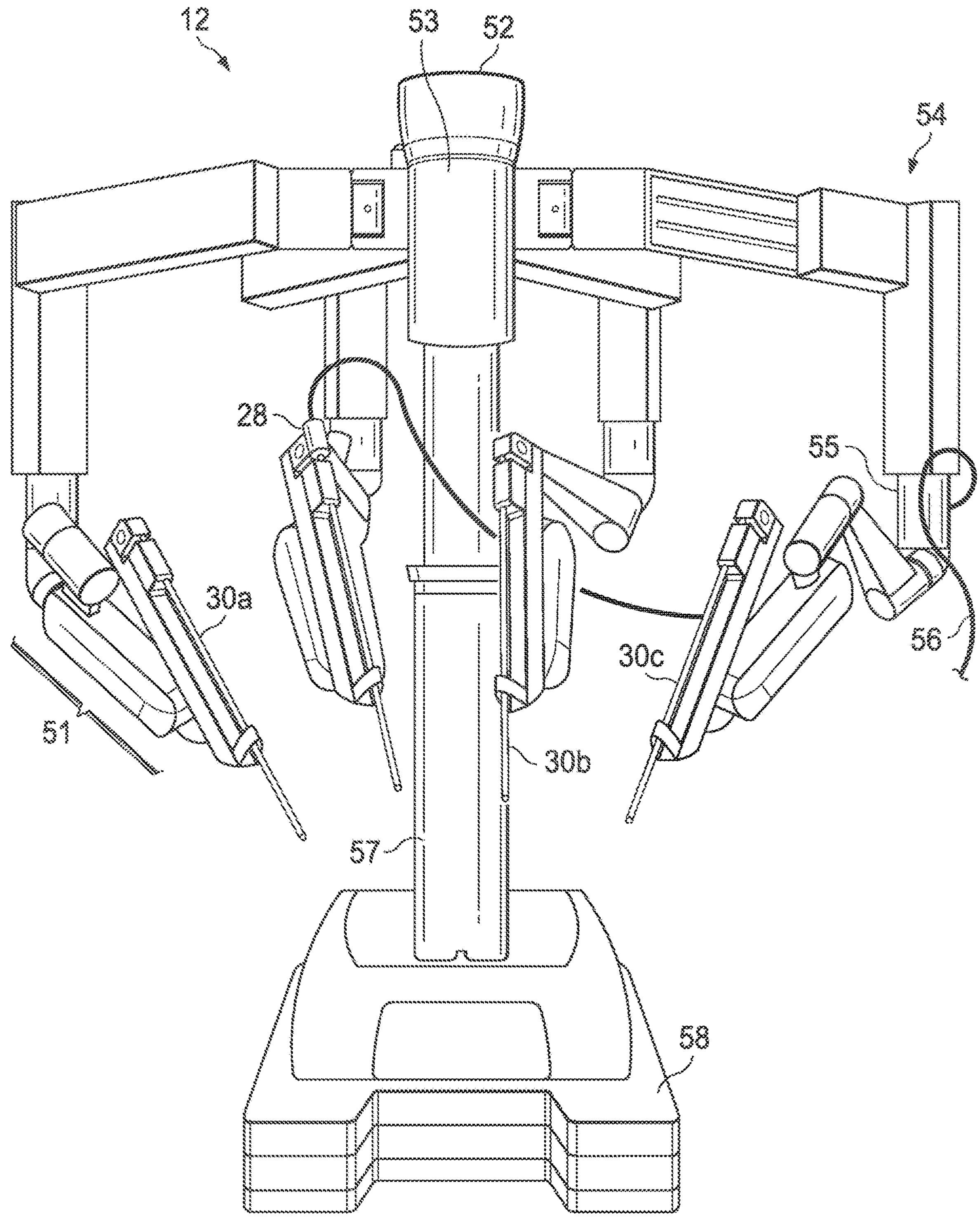
FIG. 1B is a perspective view of an assembly, in accordance with an embodiment.
Figure 1C:
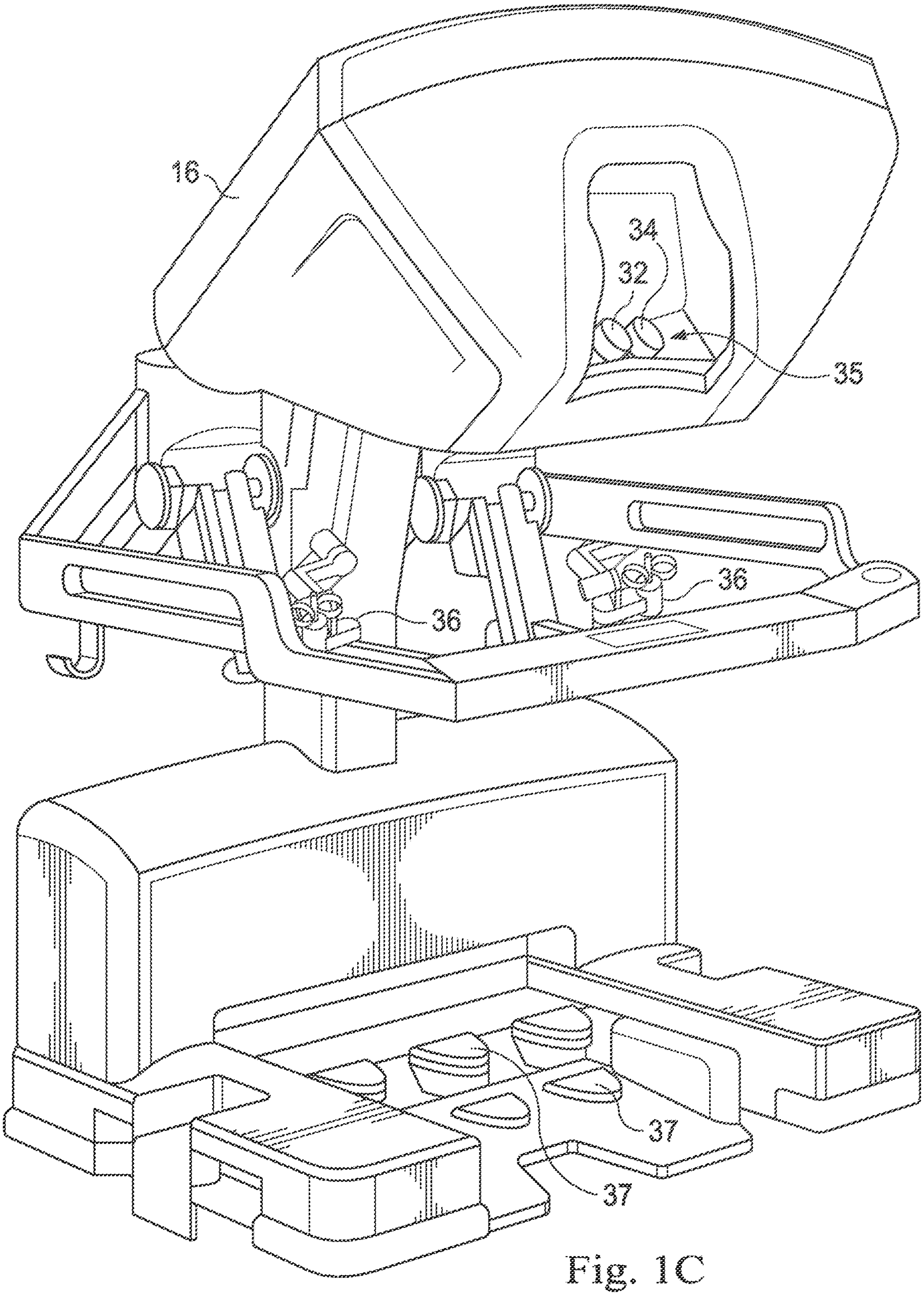
FIG. 1C is a perspective view of a surgeon's control console for a medical system, in accordance with an embodiment.

Referring now to the drawings, FIGS. 1A, 1B, and 1C together provide an overview of a medical system 10 that may be used in, for example, medical procedures including diagnostic, therapeutic, or surgical procedures. The medical system 10 is located in a medical environment 11. The medical environment 11 is depicted as an operating room in FIG. 1A. In other embodiments, the medical environment 11 may be an emergency room, a medical training environment, a medical laboratory, or some other type of environment in which any number of medical procedures or medical training procedures may take place. In still other embodiments, the medical environment 11 may include an operating room and a control area located outside of the operating room.

In one or more embodiments, the medical system 10 may be a teleoperational medical system that is under the teleoperational control of a surgeon. In alternative embodiments, the medical system 10 may be under the partial control of a computer programmed to perform the medical procedure or sub-procedure. In still other alternative embodiments, the medical system 10 may be a fully automated medical system that is under the full control of a computer programmed to perform the medical procedure or sub-procedure with the medical system 10. One example of the medical system 10 that may be used to implement the systems and techniques described in this disclosure is the da Vinci® Surgical System manufactured by Intuitive Surgical, Inc. of Sunnyvale, California.

As shown in FIG. 1A, the medical system 10 generally includes an assembly 12, which may be mounted to or positioned near an operating table O on which a patient P is positioned. The assembly 12 may be referred to as a patient side cart, a surgical cart, or a surgical robot. In one or more embodiments, the assembly 12 may be a teleoperational assembly. The teleoperational assembly may be referred to as, for example, a teleoperational arm cart. A medical instrument system 14 and an endoscopic imaging system 15 are operably coupled to the assembly 12. An operator input system 16 allows a surgeon S or other type of clinician to view images of or representing the surgical site and to control the operation of the medical instrument system 14 and/or the endoscopic imaging system 15.

The medical instrument system 14 may comprise one or more medical instruments. In embodiments in which the medical instrument system 14 comprises a plurality of medical instruments, the plurality of medical instruments may include multiple of the same medical instrument and/or multiple different medical instruments. Similarly, the endoscopic imaging system 15 may comprise one or more endoscopes. In the case of a plurality of endoscopes, the plurality of endoscopes may include multiple of the same endoscope and/or multiple different endoscopes.

The operator input system 16 may be located at a surgeon's control console, which may be located in the same room as operating table O. In some embodiments, the surgeon S and the operator input system 16 may be located in a different room or a completely different building from the patient P. The operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and other types of input devices.

In some embodiments, the control device(s) will be provided with the same degrees of freedom as the medical instrument(s) of the medical instrument system 14 to provide the surgeon with telepresence, which is the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices that move with six degrees of freedom, and which may also include an actuatable handle for actuating instruments (for example, for closing grasping jaw end effectors, applying an electrical potential to an electrode, delivering a medicinal treatment, and actuating other types of instruments).

The assembly 12 supports and manipulates the medical instrument system 14 while the surgeon S views the surgical site through the operator input system 16. An image of the surgical site may be obtained by the endoscopic imaging system 15, which may be manipulated by the assembly 12. The assembly 12 may comprise endoscopic imaging systems 15 and may similarly comprise multiple medical instrument systems 14 as well. The number of medical instrument systems 14 used at one time will generally depend on the diagnostic or surgical procedure to be performed and on space constraints within the operating room, among other factors. The assembly 12 may include a kinematic structure of one or more non-servo controlled links (e.g., one or more links that may be manually positioned and locked in place, generally referred to as a set-up structure) and a manipulator. When the manipulator takes the form of a teleoperational manipulator, the assembly 12 is a teleoperational assembly. The assembly 12 includes a plurality of motors that drive inputs on the medical instrument system 14. In an embodiment, these motors move in response to commands from a control system (e.g., control system 20). The motors include drive systems which when coupled to the medical instrument system 14 may advance a medical instrument into a naturally or surgically created anatomical orifice. Other motorized drive systems may move the distal end of said medical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors may be used to actuate an articulable end effector of the medical instrument for grasping tissue in the jaws of a biopsy device or the like. Medical instruments of the medical instrument system 14 may include end effectors having a single working member such as a scalpel, a blunt blade, an optical fiber, or an electrode. Other end effectors may include, for example, forceps, graspers, scissors, or clip appliers.

The medical system 10 also includes a control system 20. The control system 20 includes at least one memory 24 and at least one processor 22 for effecting control between the medical instrument system 14, the operator input system 16, and other auxiliary systems 26 which may include, for example, imaging systems, audio systems, fluid delivery systems, display systems, illumination systems, steering control systems, irrigation systems, and/or suction systems. A clinician may circulate within the medical environment 11 and may access, for example, the assembly 12 during a set up procedure or view a display of the auxiliary system 26 from the patient bedside.

Though depicted as being external to the assembly 12 in FIG. 1A, the control system 20 may, in some embodiments, be contained wholly within the assembly 12. The control system 20 also includes programmed instructions (e.g., stored on a non-transitory, computer-readable medium) to implement some or all of the methods described in accordance with aspects disclosed herein. While the control system 20 is shown as a single block in the simplified schematic of FIG. 1A, the control system 20 may include two or more data processing circuits with one portion of the processing optionally being performed on or adjacent the assembly 12, another portion of the processing being performed at the operator input system 16, and the like.

Any of a wide variety of centralized or distributed data processing architectures may be employed. Similarly, the programmed instructions may be implemented as a number of separate programs or subroutines, or they may be integrated into a number of other aspects of the systems described herein, including teleoperational systems. In one embodiment, the control system 20 supports wireless communication protocols such as Bluetooth, IrDA, HomeRF, IEEE 802.11, DECT, and Wireless Telemetry.

The control system 20 is in communication with a database 27 which may store one or more clinician profiles, a list of patients and patient profiles, a list of procedures to be performed on said patients, a list of clinicians scheduled to perform said procedures, other information, or combinations thereof. A clinician profile may comprise information about a clinician, including how long the clinician has worked in the medical field, the level of education attained by the clinician, the level of experience the clinician has with the medical system 10 (or similar systems), or any combination thereof.

The database 27 may be stored in the memory 24 and may be dynamically updated. Additionally or alternatively, the database 27 may be stored on a device such as a server or a portable storage device that is accessible by the control system 20 via an internal network (e.g., a secured network of a medical facility or a teleoperational system provider) or an external network (e.g. the Internet). The database 27 may be distributed throughout two or more locations. For example, the database 27 may be present on multiple devices which may include the devices of different entities and/or a cloud server. Additionally or alternatively, the database 27 may be stored on a portable user-assigned device such as a computer, a mobile device, a smart phone, a laptop, an electronic badge, a tablet, a pager, and other similar user devices.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, assembly 12. In some embodiments, the servo controller and assembly 12 are provided as part of a teleoperational arm cart positioned adjacent to the patient's body.

The control system 20 can be coupled with the endoscopic imaging system 15 and can include a processor to process captured images for subsequent display, such as to a surgeon on the surgeon's control console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

In alternative embodiments, the medical system 10 may include more than one assembly 12 and/or more than one operator input system 16. The exact number of assemblies 12 will depend on the surgical procedure and the space constraints within the operating room, among other factors. The operator input systems 16 may be collocated or they may be positioned in separate locations. Multiple operator input systems 16 allow more than one operator to control one or more assemblies 12 in various combinations. The medical system 10 may also be used to train and rehearse medical procedures.

FIG. 1B is a perspective view of one embodiment of an assembly 12 which may be referred to as a patient side cart, surgical cart, teleoperational arm cart, or surgical robot. The assembly 12 shown provides for the manipulation of three surgical tools 30*a*, 30*b*, and 30*c* (e.g., medical instrument systems 14) and an imaging device 28 (e.g., endoscopic imaging system 15), such as a stereoscopic endoscope used for the capture of images of the site of the procedure. The imaging device may transmit signals over a cable 56 to the control system 20. Manipulation is provided by teleoperative mechanisms having a number of joints. The imaging device 28 and the surgical tools 30*a-c* can be positioned and manipulated through incisions in the patient so that a kinematic remote center is maintained at the incision to minimize the size of the incision. Images of the surgical site can include images of the distal ends of the surgical tools 30*a-c* when they are positioned within the field-of-view of the imaging device 28.

The assembly 12 includes a drivable base 58. The drivable base 58 is connected to a telescoping column 57, which allows for adjustment of the height of arms 54. The arms 54 may include a rotating joint 55 that both rotates and moves up and down. Each of the arms 54 may be connected to an orienting platform 53. The arms 54 may be labeled to facilitate trouble shooting. For example, each of the arms 54 may be emblazoned with a different number, letter, symbol, other identifier, or combinations thereof. The orienting platform 53 may be capable of 360 degrees of rotation. The assembly 12 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument, e.g., one of the surgical tools 30*a-c*. The manipulator arms 51 may be teleoperatable. In some examples, the arms 54 connecting to the orienting platform 53 may not be teleoperatable. Rather, such arms 54 may be positioned as desired before the surgeon S begins operation with the teleoperative components. Throughout a surgical procedure, medical instruments may be removed and replaced with other instruments such that instrument to arm associations may change during the procedure.

Endoscopic imaging systems (e.g., endoscopic imaging system 15 and imaging device 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

FIG. 1C is a perspective view of an embodiment of the operator input system 16 at the surgeon's control console. The operator input system 16 includes a left eye display 32 and a right eye display 34 for presenting the surgeon S with a coordinated stereo view of the surgical environment that enables depth perception. The left and right eye displays 32, 32 may be components of a display system 35. In other embodiments, the display system 35 may include one or more other types of displays.

The operator input system 16 further includes one or more input control devices 36, which in turn cause the assembly 12 to manipulate one or more instruments of the endoscopic imaging system 15 and/or medical instrument system 14. The input control devices 36 can provide the same degrees of freedom as their associated instruments to provide the surgeon S with telepresence, or the perception that the input control devices 36 are integral with said instruments so that the surgeon has a strong sense of directly controlling the instruments. To this end, position, force, and tactile feedback sensors (not shown) may be employed to transmit position, force, and tactile sensations from the medical instruments, e.g., surgical tools 30*a-c*, or imaging device 28, back to the surgeon's hands through the input control devices 36. Input control devices 37 are foot pedals that receive input from a user's foot. Aspects of the operator input system 16, the assembly 12, and the auxiliary systems 26 may be adjustable and customizable to meet the physical needs, skill level, or preferences of the surgeon S.

During a medical procedure performed using the medical system 10, the surgeon S or another clinician may need to manipulate tissue to retract the tissue, expose a target area, inspect a hidden region of tissue, or perform some other action. For example, the surgeon S may need to use the surgical tool 30*a* to retract the tissue but the instrument may be partially or fully outside the field of view of the endoscopic imaging system 15. Thus, the surgeon S may be unable to readily observe whether or not movement of the surgical tool 30*a* would cause a collision with the surgical tool 30*b*, the surgical tool 30*c*, or one of the manipulator arms 51. Further, the surgeon S may need to contort his or her wrist in order to take control of the surgical tool 30*a*. Thus, it may be desirable to have methods and systems that improve the surgeon S's experience of manipulating tissue during a medical procedure.

The various embodiments described below provide methods and systems that allow the surgeon S to more easily and directly manipulate tissue within the field of view of the endoscopic imaging system 15 using an instrument (e.g. one of the surgical tools 30*a*, 30*b*, or 30*c*). In one or more embodiments, the display system 35 may display a tissue control point (e.g. tissue control point 200 in FIG. 2 below) over an image representing the field of view of the endoscopic imaging system 15. The surgeon S may manipulate the tissue control point 200 using the operator input system 16 and the control system 20 may process this input to thereby control operation of the instrument. The use of the tissue control point 200 simplifies the steps needed by the surgeon S to manipulate the tissue in a desired manner. Further, using the tissue control point 200 allows the surgeon S to control operation of the instrument to thereby manipulate tissue in the field of view of the endoscopic imaging system 15 even when the instrument is partially or fully out of the field of view.

Figure 2:
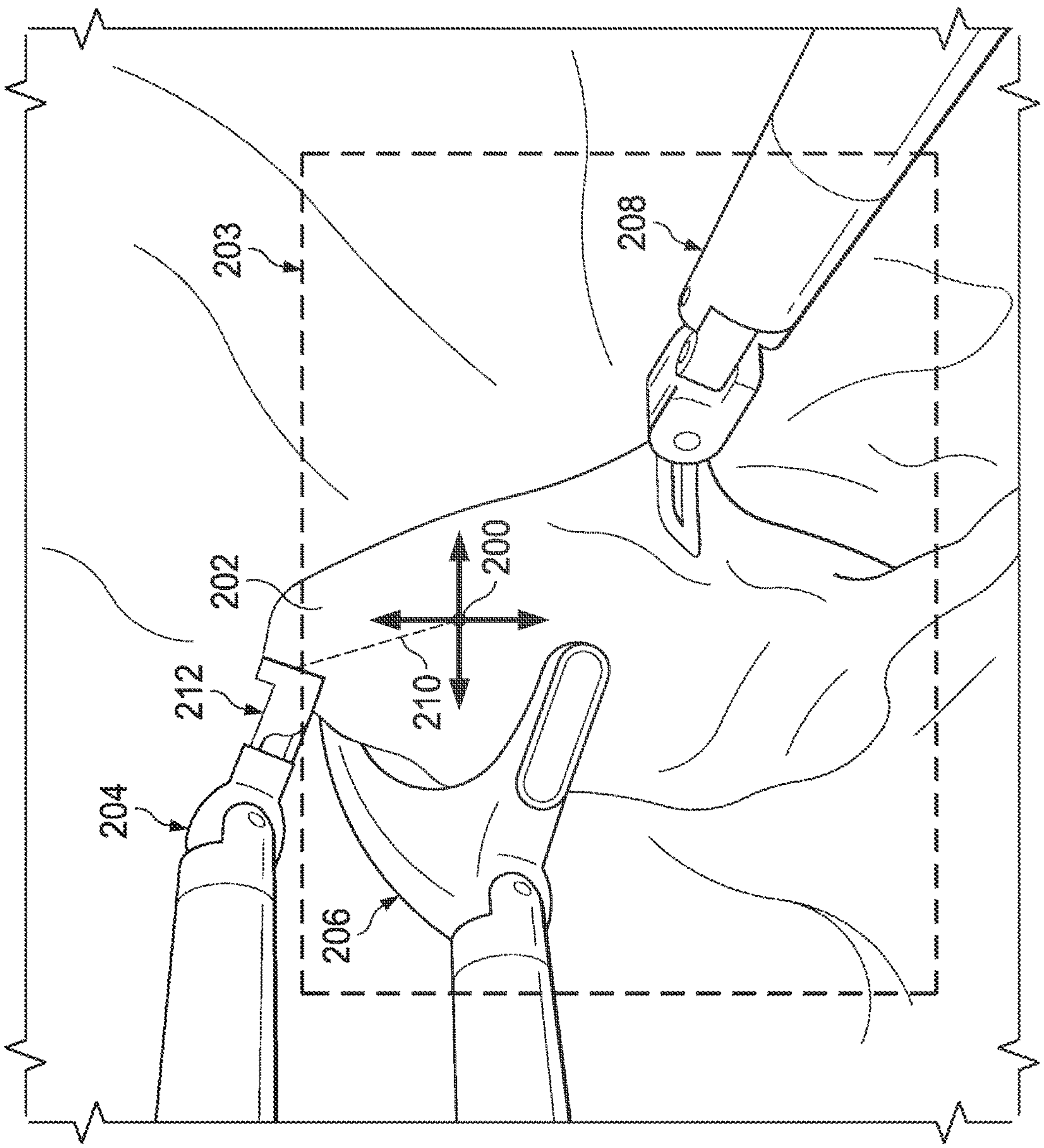
FIG. 2 is a representational diagram of a tissue control point collocated with tissue to be controlled using the tissue control point, in accordance with an embodiment.

FIG. 2 is a representational diagram of a tissue control point 200 that is collocated with the tissue 202 to be controlled using the tissue control point 200. This diagram depicts a boundary 203 that represents the field of view of the endoscopic imaging system 15. This field of view would be displayed as an image of the tissue 202 in a user interface on the display system 35. The image may be an image of or an image representing the field of view of the endoscopic imaging system 15.

The diagram further depicts an instrument 204, an instrument 206, and an instrument 208, each of which is engaged with the tissue. Each of the instrument 204, the instrument 206, and the instrument 208 may be an example of one type of instrument that may be in a medical instrument system, such as medical instrument system 14 in FIG. 1. For example, in one embodiment, the instrument 204, the instrument 206, and the instrument 208 may be surgical tools 30*a*, 30*b*, and 30*c* in FIG. 1B. The instrument 204 may be used to manipulate the tissue 202 during the medical procedure. The instrument 204 may be used to perform tasks such as, for example, retraction, countertraction, or a combination thereof. For example, the instrument 204 may be implemented as a retractor, a grasper, forceps, clamps, or some other type of auxiliary instrument.

The tissue control point 200 may be movable within the user interface displayed on the display system 35 in FIG. 1C relative to the image of the tissue and may be movable with a selected number of degrees of freedom. For example, the tissue control point 200 may be translatable, rotatable, or both. In one or more embodiment, the tissue control point 200 is implemented as a graphical element (e.g. a movable indicator) that indicates the number of degrees of freedom with which the tissue control point 212 may be moved. In some embodiments, the tissue control point 212 may be translated or rotated in any direction relative to the user interface 210.

In one embodiment, the tissue control point 200 is represented using a four-headed arrow cursor. This four-headed arrow cursor indicates that the tissue control point 200 is movable in four translational directions (e.g. left, right, up, and down). The tissue control point 200 may be used to control the instrument 204. As depicted, the instrument 204 may be located outside the boundary 203 representing the field of view of the endoscopic imaging system 15. The tissue control point 200 enables the surgeon S or other clinician to control operation of the instrument 204 even when the instrument 204 is not visible in the field of view, and thereby not displayed in the user interface. An offset 210 is present between the tip 212 and the tissue control point 200. The offset 210 is represented by a dotted-line that extends between a tip 212 of the instrument 204 and the tissue control point 200.

Figure 3:
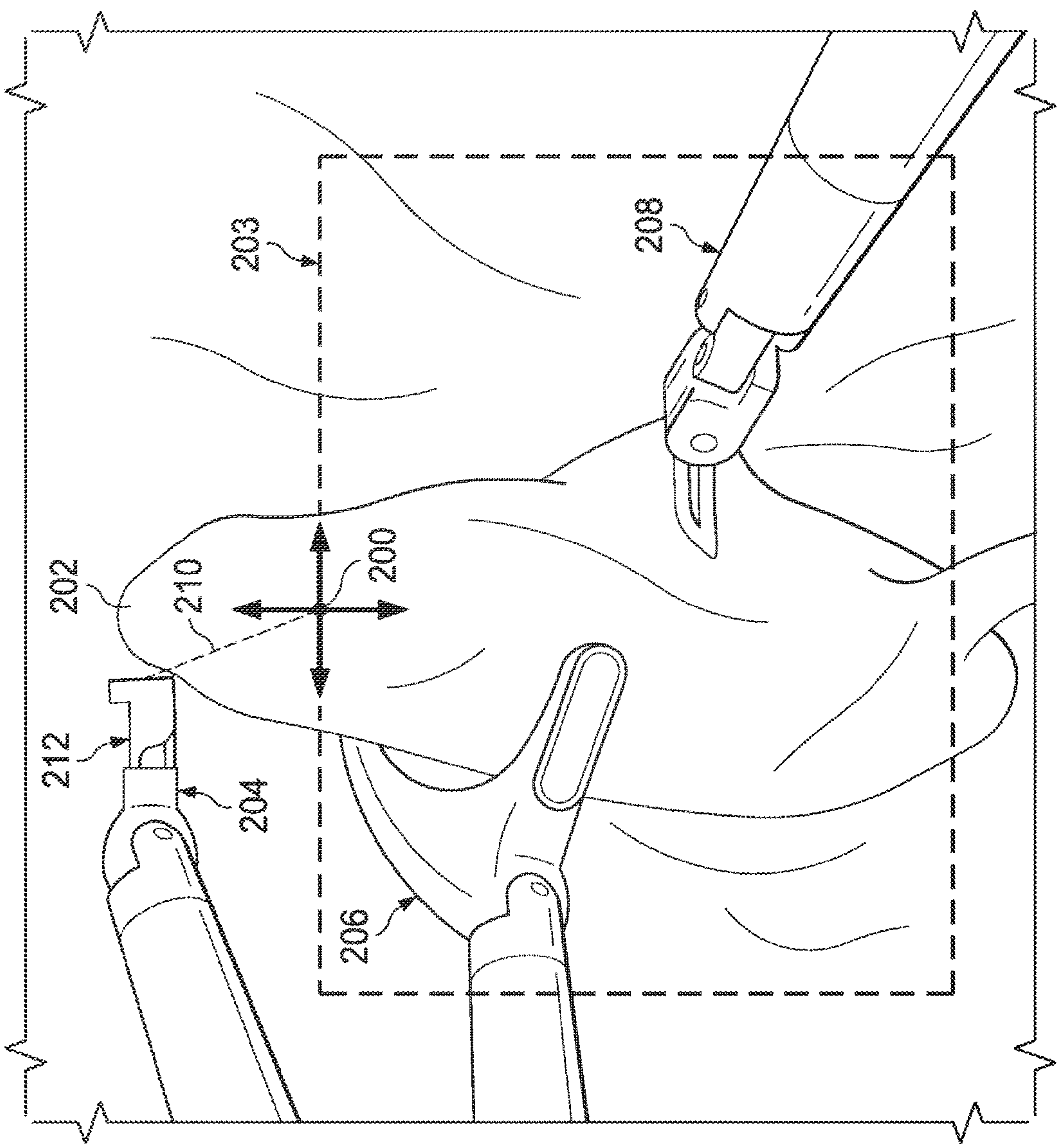
FIG. 3 is the representation diagram of the tissue from FIG. 7 after the tissue has been manipulated based on movement of the tissue control point, in accordance with an embodiment.
Figure 7:
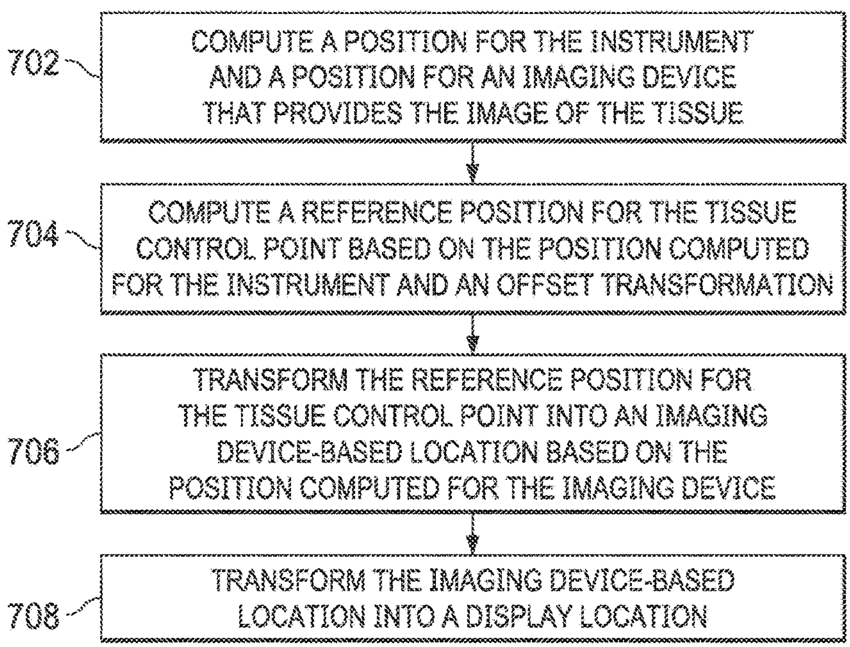
FIG. 7 is a flowchart illustrating a method for virtually collocating the tissue control point with the tissue to be controlled, in accordance with an embodiment.

FIG. 3 is the representation diagram of the tissue 202 from FIG. 7 after the tissue 202 has been manipulated based on movement of the tissue control point 200. As depicted, the tissue control point 200 has been translated upwards. Based on this movement, the control system 20 operates the instrument 204 to cause a corresponding movement of the instrument 204, which thereby manipulates the tissue.

Figure 4:
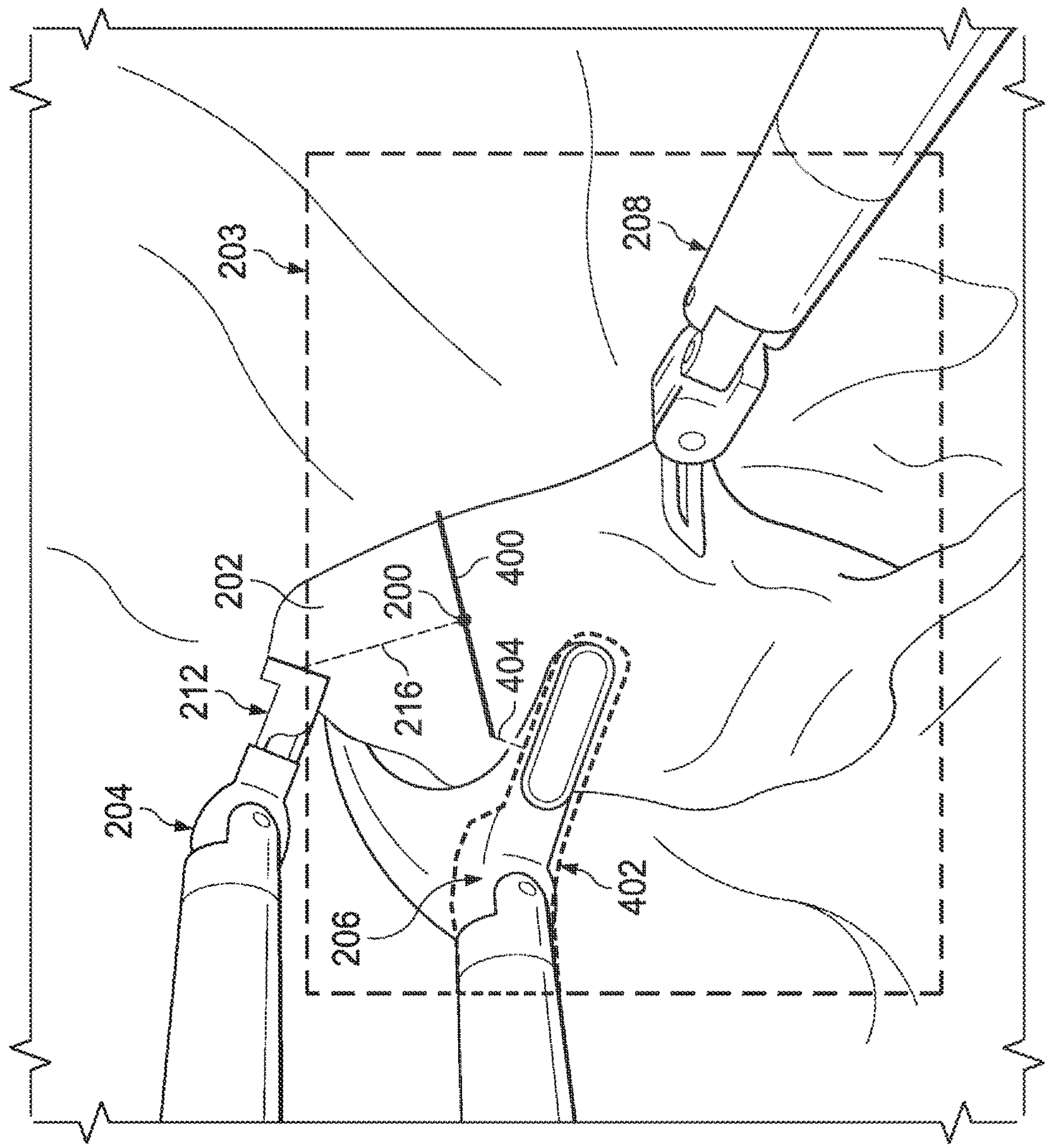
FIG. 4 is a representational diagram of a tissue control point represented as a virtual object or fixture that is collocated with tissue on which a medical procedure is being performed in accordance with an embodiment.

FIG. 4 is the representational diagram of the tissue control point 200 represented as a virtual object 400 (or virtual fixture) that is collocated with the tissue 202 to be controlled. In FIG. 4, the virtual object 400 is depicted as a graphical line element. The proxy geometry 402 of the instrument 206 may be known to the control system 20. The proxy geometry 402 may indicate the geometry of the jaws of the instrument 206, the tip of the instrument 206, or some other portion of the instrument 206. In this embodiment, the proxy geometry 402 indicates the geometry of the jaws of the instrument 206. A distance 404 is represented by a dotted-line that extends between the proxy geometry 402 and the virtual object 400. When the proxy geometry 402 and virtual object 400 are not in contact, the distance 404 represents the closest distance between the proxy geometry 402 and the virtual object 400. When the proxy geometry 402 and the virtual object 400 are in contact, the distance 404 represents a penetration depth, which may be used for rendering a restoring force.

Figure 5:
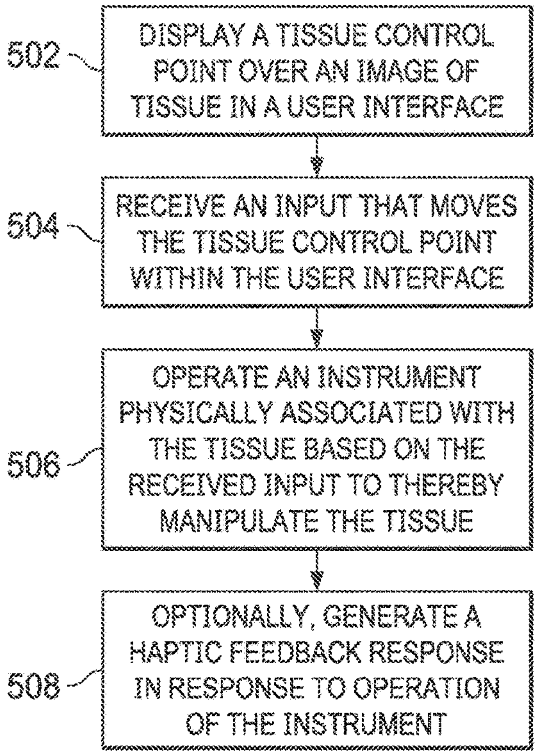
FIG. 5 is a flowchart illustrating a method for manipulating tissue, in accordance with an embodiment.

FIG. 5 is a flowchart of a method 500 for manipulating tissue. The method 500 is illustrated in FIG. 3 as a set of operations or processes 502 through 508 and is described with continuing reference to FIGS. 1A, 1B, 1C, and 2. Not all of the illustrated processes 502 through 508 may be performed in all embodiments of method 500. Additionally, one or more processes that are not expressly illustrated in FIG. 3 may be included before, after, in between, or as part of the processes 502 through 508. In some embodiments, one or more of the processes 502 through 508 may be implemented, at least in part, in the form of executable code stored on non-transitory, tangible, machine-readable media that when run by one or more processors (e.g., the processors of control system) may cause the one or more processors to perform one or more of the processes.

At process 502, the tissue control point 200 is displayed over the image of the tissue 202 in the user interface. The tissue control point 200 may be a graphical indicator that allows a user (e.g. the surgeon S) to control the instrument 204 engaged with the tissue 202 of the patient during the medical procedure to thereby manipulate the tissue 202. The instrument 204 may be engaged with the tissue 202 by being physically associated with the tissue 202. For example, the instrument may be touching the tissue 202, grasping the tissue 202, retracting the tissue 202, applying a force to the tissue 202, otherwise engaging the tissue 202, or a combination thereof. The image of the tissue 202 may be provided by, for example, the endoscopic imaging system 15 in FIG. 1A. In other words, the image may present the field of view of the endoscopic imaging system 15.

The tissue control point 200 is displayed over the image at a selected location over the tissue 202 in the image. In this manner, the tissue control point 200 may be considered virtually collocated with the tissue 202. The selected location for the tissue control point 200 may be established based on a position of the instrument 204 relative to the tissue. In some cases, the instrument 204 may be visible in the image. In other cases, the instrument 204 may not be visible in the image. In other words, the instrument 204 may be out of a field of view of the endoscopic imaging system 15. In cases where the instrument 204 is out of the field of view, the selected location for the tissue control point 200 relative to the image may be offset from a position of the instrument 204 or tip 212 of the instrument 204 relative to the tissue 202.

At process 504, an input is received that moves the tissue control point 200 within the user interface. This input may be received through the input control device 36 and processed by the control system 20. In some embodiments, the input device 208 may be a joystick. In other embodiments, the input control device 36 may include at least one of a touchscreen, a gesture tracking system, a gaze tracking system, a hand control device, a teleoperated device, a mouse, or some other type of input device such as described for input devices 36, 37.

Based on the received input, the control system 20 may move the tissue control point 200. The tissue control point 200 may have a selected number of degrees of freedom. The number of degrees of freedom selected may be task-specific based on the types of corresponding movements that need to be provided for the instrument 204. The human arm is considered to have seven degrees of freedom. In one embodiment, the number of degrees of freedom selected for the tissue control point 200 is less than the seven degrees of freedom provided by the human arm to thereby simplify the user interactions needed to achieve the desired movement of the instrument 204.

In one embodiment, movement of the tissue control point 200 may include a left translation, a right translation, an upward translation, a downward translation, an inward translation, an outward translation, a rotation of the tissue control point, or a combination thereof. The translation of the tissue control point 200 depicted in FIG. 3 is an example of one type of movement of the tissue control point 200 based on the received input. In some embodiments, movement of the tissue control point 200 may include multiple translations in varying directions and/or the same direction. In other embodiments, the tissue control point 200 may be only translatable, only translatable along one axis, only rotatable, or limited in movement in some other manner. In one embodiment, when the instrument 204 has jaws that grasp the tissue 202, movement of the tissue control point 200 may be restricted such that the tissue control point 200 cannot cause the jaws to open and release the tissue 202.

At process 506, the instrument 204, which is physically associated with the tissue 202, is operated based on the received input to thereby manipulate the tissue 202. In one embodiment, operating the instrument 204 includes transforming the movement of the tissue control point 200 into a corresponding movement for the instrument 204 to thereby manipulate the tissue 202. This transformation may take into account factors in addition to the movement of the tissue control point 200.

For example, the transformation may include optimizing movement of the instrument 204 based on one or more secondary objectives. These secondary objectives may include optimizing a speed of movement, ensuring that the movement is within selected range of motion limits for the instrument 204, avoiding collision with one or more other instruments or structures, creating sufficient working space between the instrument 204 and any neighboring instruments, avoiding selected areas or zones (e.g. keep-out zones), or a combination thereof. In one or more embodiments, the control system 20 determines the position of the instrument 204 and the manipulator arm (e.g. manipulator arm 51) connected to the instrument relative to other instruments and manipulator arms. The control system 20 may compute a path of movement for the instrument 204 that both corresponds to the movement of the tissue control point 200 and prevents interaction of the different instruments and manipulator arms. The path of movement may include any number of translational movements, rotational movements, or combination thereof.

In some embodiments, the control system 20 may identify operational parameters for the instrument 204. These operational parameters may include for example, a geometry, a minimum speed of movement, a maximum speed of movement, a range of motion, a number of degrees of freedom, other types of parameters, or a combination thereof for the instrument 204. The control system 20 may compute a path of movement for the instrument 204 that takes into account these optional parameters. Further, the control system 20 may compute a path of movement for the instrument 204 that ensures that the instrument 204 does not enter selected areas or zones (e.g. keep-out zones).

In some embodiments, the control system 20 may impose limits on the amount of force the instrument 204 is allowed to exert. For example, the instrument 204 may be generally capable of exerting about 2 pounds of force at the tip 212 of the instrument 204. The control system 20, however, may limit the amount of force that can be exerted at the tip 212 of the instrument 204 to about 0.5 pounds of force.

In one or more embodiments, operating the instrument 204 at process 506 manipulates the tissue 202 by causing a corresponding movement of the tissue 202 that achieves both the intended movement of the instrument 204 as well as the secondary objectives. The corresponding movement of the tissue 202 may be, for example, a retraction of the tissue 202, a translation of the tissue 202, a twisting of the tissue 202, a rotation of the tissue 202, a deformation of the tissue 202, or a combination thereof. In this manner, movement of the tissue control point 200 by the user through the input control device 36 may be transformed into a corresponding movement of the instrument 204 that results in the tissue 202 engaged with or near the instrument 204 being retracted, twisted, rotated, lifted, pushed down, pulled downwards, raised upwards, moved to the side, moved upwards, deformed, and/or otherwise manipulated.

In some embodiments, the control system 20 may use imaging data or sensor data to observe movement of the tissue 202 surrounding the tissue control point 200 and may update the one or more control laws used in controlling movement of the instrument 204 based on the movement of the tissue control point 200 to reduce errors in the observed movement of the tissue 202. In other words, the control system 20 may use feedback in the form of imaging data or sensor data to reduce errors in the actual motion of the tissue 202 relative to the intended motion of the tissue 202 based on the movement of the tissue control point 200.

At process 508, which may be optional, a haptic feedback response is generated in response to operation of the instrument 204. The haptic feedback response, which may be also referred to as a haptic communication or a kinesthetic response, may be a physical or mechanical stimulation through the application of forces, vibrations, motion, or a combination thereof to the user. The haptic feedback response may be generated based on a physical effect of the operation of the instrument 204 on the tissue 202 and may allow the user to receive information from the control system 20 in the form of a felt sensation on some part of the body. The haptic feedback response may, for example, allow the user to experience the stiffness, rigidity, or deformability of the tissue 202. In some embodiments, the haptic feedback response may allow the user to experience traction and resistance of the tissue 202 to movement.

The haptic feedback response may be generated using a haptic device that generates tactile sensations that can be felt by the user. The haptic device may include at least one of a teleoperated device, a joystick, gloves, some other type of hand control device, some other type of tactile sensation generating device, or combination thereof. In some embodiments, the haptic device may be the input control device 36. For example, the input control device 36 may reflect forces and torques generated from virtual-physical interactions through physical force. The virtual-physical interactions may be, for example, the encountering of constraints due to contact with virtual surfaces, virtual lines, virtual points, or a combination thereof.

Figure 6:
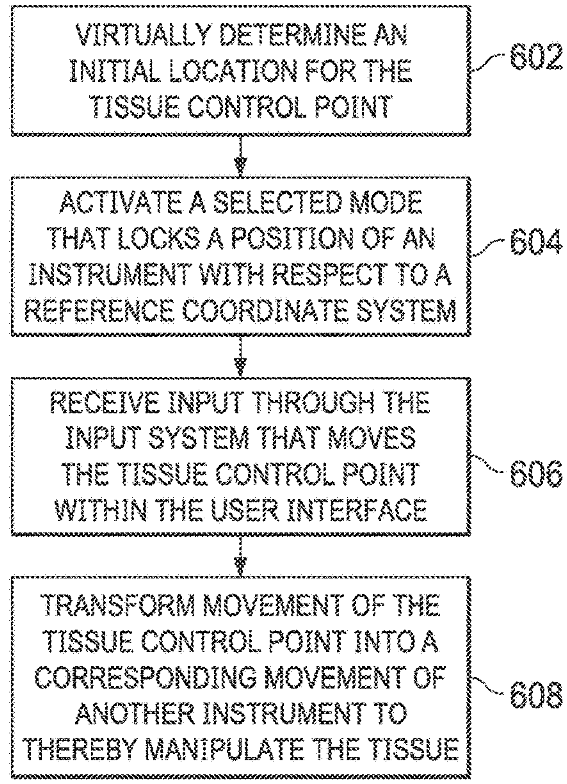
FIG. 6 is a flowchart illustrating a method for manipulating tissue, in accordance with an embodiment.

FIG. 6 is an illustration of a method 600 for manipulating tissue. The method 600 is illustrated as a set of operations or processes 602 through 608 and is described with continuing reference to FIGS. 1A, 1B, 1C, and 2. Not all of the illustrated processes 602 through 608 may be performed in all embodiments of method 600. Additionally, one or more processes that are not expressly illustrated in FIG. 6 may be included before, after, in between, or as part of the processes 602 through 608. In some embodiments, one or more of the processes 602 through 608 may be implemented, at least in part, in the form of executable code stored on non-transitory, tangible, machine-readable media that when run by one or more processors (e.g., the processors of control system) may cause the one or more processors to perform one or more of the processes.

At process 602, an initial location for the tissue control point 200 is virtually determined. Determining this initial location includes establishing a relationship between the tissue 202 to be controlled, the tissue control point 200, and the instrument 204. More specifically, determining this initial location includes establishing a relationship between the tissue 202 to be controlled, the tissue control point 200, and a tip or end effector of the instrument 204.

In one embodiment, the initial location for the tissue control point 200 may be determined or selected by the user. For example, the user may enter initial input that is used to determine the tissue control point 200. The user may select the initial location using, for example, the tip 212 of the instrument 204 or some other teleoperated instrument or tool to contact a location on the surface of the tissue 202 and then engage a control. Engaging the control may include, for example, pressing a button on the input control device 36. The initial location for the tissue control point may then be determined based on the location on the surface at which the tip 212 of the instrument 204 has engaged the tissue 202. In some embodiments, the instrument 204 may be used to grasp the tissue 202. The control system 20 may use the grasping force commanded to the instrument 204 for grasping the tissue 202 as a signal to establish and lock an offset between the tip 212 of the instrument 204 and the tissue control point 200.

In response to the control being engaged, the control system 20 may then create and display the tissue control point 200 at a corresponding virtual location over the image. In other embodiments, the user may use the input control device 36 to manually move the tissue control point 200 in the user interface into the selected location on the image. In still other embodiments, the input control device 36 may track or detect the gaze of the user to determine where to position the tissue control point 200. For example, the control system 20 may establish the tissue control point 200 at a location on the surface of the tissue 202 at which a gaze of the user is detected as being directed for a selected period of time. Gaze input from the left and right eyes of the user may be triangulated to produce a three-dimensional fixed location.

In one embodiment, the initial location or the tissue control point 200 may be determined by the control system 20. For example, the control system 20 may generate a sparse or dense three-dimensional surface reconstruction of a surface of the tissue 202 based on imaging data received from an imaging system (e.g. a laser imaging system). The control system 20 may then identify the location on the surface of the tissue 202 connected to or that is engaged by the instrument 204 (e.g. the tip or end effector of the instrument 204). The control system 20 may identify candidate points on the surface of the tissue 202 that are, for example, centrally located and most anterior in view and may then select the initial location for the tissue control point 200 based on the candidate points. The tissue control point 200 may be selected at a location that is visible in the field of view of the endoscopic imaging system 15, is not occluded by other instruments, and is close or optimally centered with respect to controlling the instrument 204.

In other embodiments, the three-dimensional surface reconstruction of the surface of the tissue 202 described above may be used in conjunction with the detected gaze from a single eye. For example, a vector for the gaze detected from the single eye may be intersected with the three-dimensional surface reconstruction to determine the location for the tissue control point 200.

In some embodiments, the initial location of the tissue control point 200 may be computed from a color/depth segmentation of the image provided by the endoscopic imaging system 15. For example, the control system 20 may segment a region of the image using color image segmentation or depth image segmentation. The control system 20 may then compute a centroid of the segmented region of the image as the initial location for the tissue control point 200.

In other embodiments, a two-dimensional location may be determined for the tissue control point 200 within the image. The two-dimensional location may then be mapped to a three-dimensional location with respect to a field of view of the endoscopic imaging system 15 or other imaging device that provides the image. For example, stereoscopic images displayed in the left and right eye displays 32, 32 may be processed to determine matching pixel locations in the left and right views. A depth may then be computed from the disparity between the left and right eye pixels and used to determine the three-dimensional location for the tissue control point 200. Thus, the initial location for the tissue control point 200 may be determined with reference to a two-dimensional coordinate system or a three-dimensional coordinate system.

At process 604, a selected mode is activated that locks a position of the instrument 206 with respect to a reference coordinate system. In one or more embodiments, the instrument 206 and the tissue control point 200 may be controlled using the same input control device 36 (e.g. the same joystick). Activating the selected mode configures the input control device 36 to ensure that the input received is used to control the tissue control point 200 and not the instrument 206. When the selected mode is not activated, input received through the input control device 36 is used to control the instrument 206 and not the tissue control point 200.

In other words, if a user has activated the selected mode, then the input control device 36 or some portion of the input control device 36 that is used to teleoperate the instrument 206 may be reconfigured such that input received through the input control device 36 or some portion of the input control device 36 may be used to control the tissue control point 200 rather than the instrument 206. A user may then use the input control device 36 to move the tissue control point 200, which in turn, causes corresponding operation of the instrument 204.

At process 606, input is received through the input control device 36 that moves the tissue control point 200 within the user interface. The translation of the tissue control point 2020 depicted in FIG. 3 is an example of the movement of the tissue control point 200 that occurs at process 606. At process 608, movement of the tissue control point 200 is transformed into a corresponding movement of the instrument 204 to thereby manipulate the tissue 202.

FIG. 7 is an illustration of a method 700 for virtually collocating the tissue control point 200 with the tissue 202 to be controlled. The method 700 is illustrated as a set of operations or processes 702 through 708 and is described with continuing reference to FIGS. 1A, 1B, 1C, and 2. Not all of the illustrated processes 702 through 708 may be performed in all embodiments of method 700. Additionally, one or more processes that are not expressly illustrated in FIG. 7 may be included before, after, in between, or as part of the processes 702 through 708. In some embodiments, one or more of the processes 702 through 708 may be implemented, at least in part, in the form of executable code stored on non-transitory, tangible, machine-readable media that when run by one or more processors (e.g., the processors of control system) may cause the one or more processors to perform one or more of the processes.

At process 702, a position for the instrument 204 and a position for an imaging device that provides the image of the tissue are computed. In one embodiment, at process 702, the position for the instrument 204 may be a position of a tip 212 of the instrument 204 computed using kinematic equations for the manipulator controlling the instrument 204. Similarly, the position for the imaging device (e.g. the endoscopic imaging system 15) may be a position of the tip of the imaging device computed using kinematic equations for the manipulator controlling the imaging device. A manipulator may be implemented as, for example, the manipulator arm 51 of the assembly 12 shown in FIG. 1B. The position for the tip 212 of instrument 204 may be represented by $T_{tip}$ and the position for the imaging device may be represented by $T_{imd}$. $T_{tip}$ and $T_{imd}$ may be three-dimensional transformation matrices composed of three-dimensional position and three-dimensional rotation components.

At process 704, a reference position for the tissue control point 200 is computed based on the position computed for the instrument 204 and an offset transformation. The offset transformation may be used to maintain an offset between the tip 212 of the instrument 204 and the tissue control point 200 to thereby allow the tissue control point 200 to become an extension of the kinematic chain of the manipulator arm 51 controlling the instrument 204. Using the offset transformation allows the tissue control point 200 to be related to the instrument 204 in a reference coordinate system for the instrument 204 or the manipulator arm 51 controlling the instrument 204. The reference position for the tissue control point 200 may be represented by $T_{TCP}$ and may be three-dimensional.

At process 706, the reference position for the tissue control point 200 is transformed into an imaging device-based position based on the position computed for the imaging device. This imaging device-based position may be in an imaging device coordinate system (e.g. a coordinate system for the endoscopic imaging system 15). The imaging device-based position may be in two-dimensions or three-dimensions. The imaging device-based position may be represented by $T_{TCP\_MM}$. At process 708, the imaging device-based position is transformed into a display position. The display position may be in a display coordinate system for the user interface. The display position may be represented by $T_{TCP\_DC}$. In some embodiments, the display position may be or may be used to compute the location of the tissue control point 200 relative to the image displayed in the user interface. Thus, the tissue control point 200 may be related to the instrument 204 in a number of different relevant coordinate systems.

Figure 8:
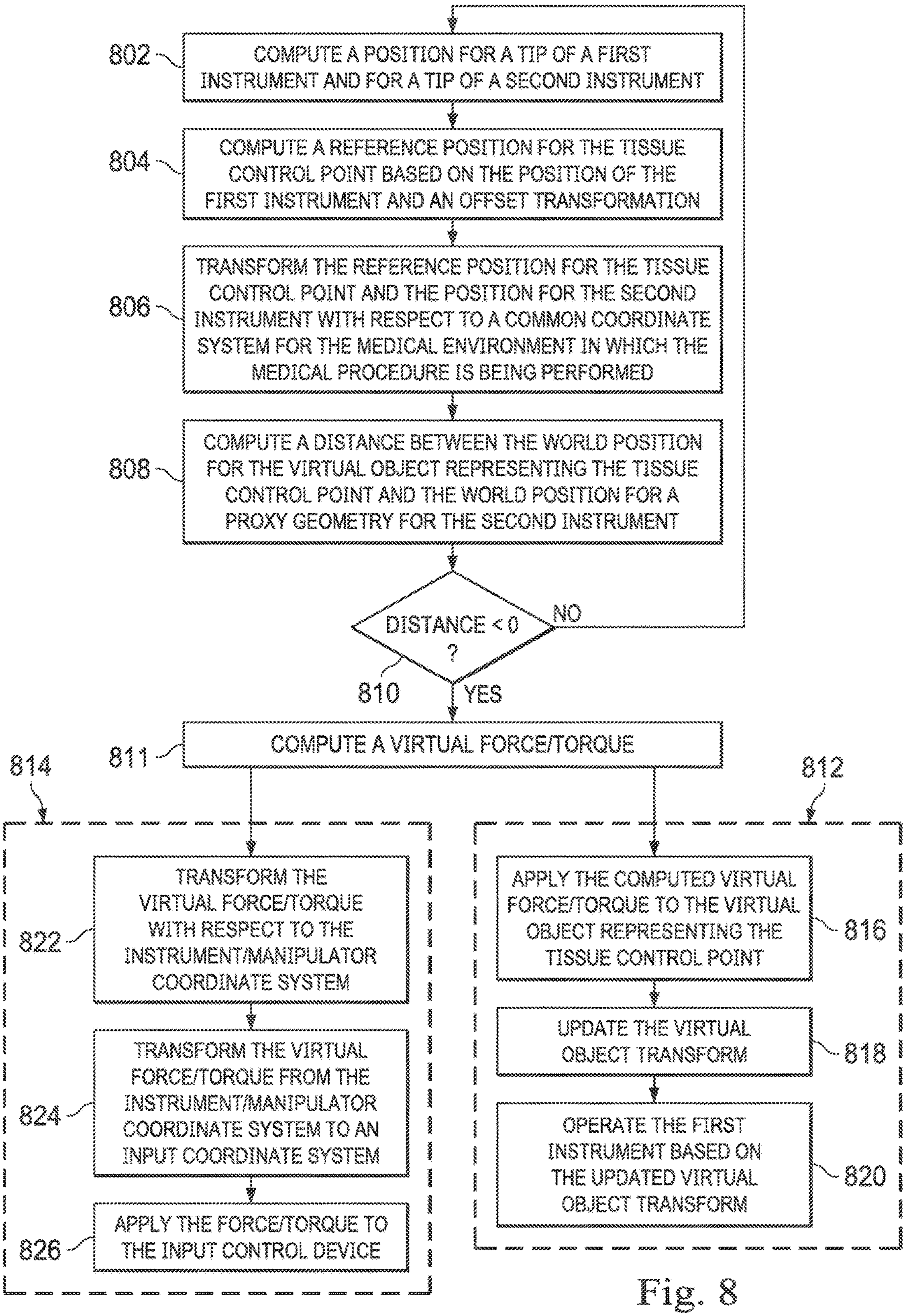
FIG. 8 is a flowchart illustrating a method for generating a haptic feedback response, in accordance with an embodiment.

FIG. 8 is an illustration of a method 800 for generating a haptic feedback response based on movement of the tissue control point 200. The method 800 is illustrated as a set of operations or processes 802 through 824 and is described with continuing reference to FIGS. 1A, 1B, 1C, and 2. Not all of the illustrated processes 802 through 824 may be performed in all embodiments of method 800. Additionally, one or more processes that are not expressly illustrated in FIG. 8 may be included before, after, in between, or as part of the processes 802 through 824. In some embodiments, one or more of the processes 802 through 824 may be implemented, at least in part, in the form of executable code stored on non-transitory, tangible, machine-readable media that when run by one or more processors (e.g., the processors of control system) may cause the one or more processors to perform one or more of the processes. In one or more embodiments, the processes 802 through 824 may be performed by the medical system 10.

At process 802, a position is computed for a tip of a first instrument 204 and a second instrument 206. An input control device 36 may be used to control the second instrument 206. In one embodiment, computing the positions at process 802 includes computing a position of the tips of the two instruments by computing, for example, the forward kinematics for the manipulator arms 51 connected to these instruments. In one or more embodiments, the input control device 36 includes, incorporates, or connects to a haptic device that provides haptic feedback. The position for the tip of the first instrument 204 may be represented by $T_{tip1}$ and the position for the tip of the second instrument 206 may be represented by $T_{tip2}$. In one or more embodiments, both $T_{tip1}$ and $T_{tip2}$ may be three-dimensional positions computed in a manipulator coordinate system using kinematic equations.

At process 804, a reference position for the tissue control point 200 is computed based on the computed position of the tip of the first instrument 204 and an offset transformation. The offset transformation may be used to maintain an offset between the tip of the instrument 204 and the tissue control point 200 to thereby allow the tissue control point 200 to become an extension of the kinematic chain of the manipulator arm 51 controlling the instrument 204. The reference position for the tissue control point 200 may be represented by $T_{TCP}$ and may be three-dimensional.

At process 806, the reference position for the tissue control point 200 and the position of the tip of the second instrument 206 are transformed with respect to a common coordinate system for the medical environment 11 in which the medical procedure is being performed. In one embodiment, the common coordinate system may be referred to as a world coordinate system. The world position for the tissue control point 200 within the world coordinate system may be represented as $T_{TCP\_WC}$, while the world position for the tip of the second input control device 36 within the world coordinate system may be represented as $T_{tip2\_WC}$. The world position for the tissue control point 200 may be the world position for the virtual object 400 representing the tissue control point 200.

The proxy geometry 402 of the second instrument 206 and the geometry of the virtual object 400 representing the tissue control point 200 may be known. The proxy geometry 402 may be moved such that the proxy geometry 402 comes into contact with or otherwise engages the virtual object 400 that represents the tissue control point 200. The proxy geometry 402 may be used to nudge, prod, or otherwise manipulate the virtual object 400. The forces exerted on the virtual object 400 by the proxy geometry 402 may affect movement of the first instrument 204, thereby causing manipulation of the tissue 202.

In other examples, the virtual object 400 may be directly grasped and manipulated using the second instrument 206. This type of control provides a natural and direct way of affecting the retracting instrument pose without having to change, for example, a control mode of the telemanipulation interface. In this manner, the user may perceive that they are using the second instrument 206 to directly move the tissue 202.

At process 808, the distance 404 between the world position for the virtual object 400 and the world position for the proxy geometry 402 for the instrument 206 is computed. As depicted in FIG. 4, the proxy geometry 402 may be the geometry of the jaws of the instrument 206. At process 810, a determination is made as to whether the distance 404 is less than zero. The distance 404 is less than zero when there is virtual penetration or interpenetration indicating virtual contact between the proxy geometry 402 and the virtual object 400. When this virtual contact exists, operation of the second instrument 206 affects the virtual object 400, which may, in turn, affect the first instrument 204, thereby causing manipulation of the tissue 202. When contact between the proxy geometry 402 and the virtual object 400 has been lost, the distance 404 is not less than zero. Without this virtual contact, operation of the second instrument 206 does not affect the virtual object 400 and thus, does not affect the first instrument 204. When the distance 404 is less than zero, the distance 404 may be referred to as a penetration depth. When the distance 404 is not less than zero, the distance 404 represents the closest distance between the proxy geometry 402 and the virtual object 400.

Referring again to the process 808, if the distance 404 is not less than zero, the method 800 returns to the process 802, as described above. But if the distance 404 is less than zero, then at process 811, a virtual force/torque is computed. The virtual force/torque may be virtual force/torque of the proxy geometry 402 on the tissue control point 200. Haptic rendering may be used to provide stable virtual contact with the tissue control point 200 and avoid a slip-through problem that happens when penetration depth exceeds the thickness of the virtual object 400.

After process 811 has been performed, sub-method 812 and sub-method 814 are performed. Sub-method 812 includes processes 816-820 for manipulating the tissue 202 via interaction with the tissue control point 200 and sub-method 814 includes processes 822-826 for providing haptic feedback to the user when interacting with the tissue control point 200.

In sub-method 812, at process 816, the computed virtual force/torque is applied to the virtual object 400 representing the tissue control point 200. The computed virtual force/torque is applied as a reaction force that moves the virtual object 400. As previously described, the virtual object 400 geometrically represents the tissue control point 200 and may be virtually collocated with the tissue 202 in the user interface. This virtual object 400 may also be referred to as a simulated tissue control point body or a simulated TCP body.

At process 818, the virtual object 400 transform is updated. This transform may be the transformation that determines how movement of the virtual object 400 by the proxy geometry 402 will affect the first instrument 204. At process 820, the first instrument 204 is operated based on the updated virtual object transform. Operation of the first instrument 204 manipulates the tissue 202. In particular, at process 820, a command for the first instrument 204 may be generated based the updated virtual object transform and then applied to (e.g. sent to) the first instrument 204. In this manner, the second instrument 206 may be operated to move the proxy geometry 402 and thereby engage and apply a force/torque on the virtual object 400. The force/torque applied to the virtual object 400 may, in turn, cause movement of the first instrument 204, which causes manipulation of the tissue 202. The force/torque may be integrated by a mass/damper virtual model to compute the corresponding velocity and change in position.

At process 822, the virtual force/torque is transformed with respect to the instrument/manipulator coordinate system. At process 824, the virtual force/torque is then transformed from the instrument/manipulator coordinate system to an input coordinate system. The input coordinate system is for the input control device 36. At process 826, the force/torque is then applied to the input control device 36. Applying the force/torque to the input control device 36 produces a haptic feedback response that may be experienced by the user. For example, the user may feel a physical response to pushing, prodding, nudging, or other motion of the tissue 202 caused by operation of the first instrument 204 based on virtual movement of the virtual object 400 by the proxy geometry 402.

In this manner, the tissue control point 200 may support familiar physical interactions by representing the tissue control point 200 as both a visual and haptic virtual object 402. Movement of the second instrument 206 may move the proxy geometry 402 so as to impart forces on the virtual object 400 representing the tissue control point 200. The force applied to the virtual object 400 may, in turn, induce movement of the first instrument 204. The determination regarding the distance 404 made at process 810 may ensure that the simulated movement of the virtual object 400 only occurs while the proxy geometry 402 is in contact with the virtual object 400. This ensures that tissue manipulation is continuously controlled by the second instrument 206 and ceases upon loss of contact between the proxy geometry 402 and the virtual object 400.

The method 800 described above provides a way in which the surgeon S or other clinician may control operation of the first instrument 204 without switching modes on the input control device 36 that is being used to control the second instrument 206. Rather, operation of the second instrument 206 may be used to virtually contact and impart forces on the virtual object 400, which then causes movement or some other type of operation of the first instrument 204.

Thus, the embodiments described above provide a method and apparatus for manipulating tissue using the tissue control point 200. The control system 20 establishes a relationship between the tissue control point 200 and the instrument 204 such that translational motion of the tissue control point 200 causes a corresponding movement of the instrument 204 that also optionally takes into account other degrees of freedom to achieve secondary objectives, such as avoiding collisions with neighboring instruments. The use of the tissue control point 200 simplifies the steps needed by a surgeon to manipulate the tissue in a desired manner. Further, using the tissue control point 200 enables the surgeon to control operation of the instrument 204 to manipulate tissue in the field of view of the endoscopic imaging system 15 even when the instrument 204 is partially or fully out of the field of view.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An apparatus comprising:

a display system configured to display an image of tissue in a user interface; and a control system communicatively coupled to the display system, wherein the control system is configured to:

display a tissue control point graphical element over the image of tissue;

receive an input that moves the tissue control point graphical element within the user interface; and operate an instrument physically associated with the tissue, based on the received input that moves the tissue control point graphical element, to thereby manipulate the tissue.

2. The apparatus of claim 1, wherein movement of the tissue control point graphical element based on the input comprises at least one of a left translation, a right translation, an upward translation, a downward translation, an inward translation, an outward translation, or a rotation of the tissue control point graphical element.

3. The apparatus of claim 1, further comprising:

an input device, wherein the input is received through the input device.

4. The apparatus of claim 3, wherein the input device comprises at least one of a touchscreen, a gesture tracking system, a gaze tracking system, a hand control device, a teleoperated device, or a mouse.

5. The apparatus of claim 1, wherein the control system is further configured to compute a path of movement for the instrument that both corresponds to movement of the tissue control point graphical element and meets predefined criteria.

6. The apparatus of claim 1, wherein movement of the tissue control point graphical element comprises at least one of a translation of the tissue control point graphical element or a rotation of the tissue control point graphical element relative to the image.

7. The apparatus of claim 1, wherein manipulation of the tissue comprises at least one of a retraction of the tissue, a translation of the tissue, or a twisting of the tissue.

8. The apparatus of claim 1, wherein the control system is further configured to generate a haptic feedback response in response to operation of the instrument.

9. The apparatus of claim 1, wherein the control system is further configured to compute a path of movement for the instrument that prevents the instrument from having an unintended interaction with another object.

10. The apparatus of claim 1, wherein the tissue control point graphical element is offset from a position of the instrument in the image.

11. The apparatus of claim 1, wherein the control system is further configured to determine an initial location for the tissue control point graphical element based on the input.

12. The apparatus of claim 1, wherein the control system is further configured to receive an initial location input through an input device after a tip of the instrument has engaged the tissue and responsive to receiving the initial location input, determine an initial location for the tissue control point graphical element based on a location at which the tip of the instrument has engaged the tissue.

13. The apparatus of claim 1, wherein the control system is further configured to determine a two-dimensional location for the tissue control point graphical element within the image; and map the two-dimensional location to a three-dimensional location with respect to a field of view of an imaging device that provides the image.

14. The apparatus of claim 1, wherein the instrument is a first instrument and wherein the control system is further configured to activate a selected mode that locks a position of a second instrument with respect to a reference coordinate system and enables the input to be received for the tissue control point graphical element.

15. The apparatus of claim 14, wherein the control system is further configured to receive the input that moves the tissue control point graphical element within the user interface through an input device when the selected mode has been activated, wherein the input device controls movement of the first instrument when the selected mode is activated and controls movement of the second instrument when the selected mode is not activated.

16. The apparatus of claim 1, further comprising the instrument.

17. An apparatus comprising:

a display system configured to display an image of tissue in a user interface; and a control system communicatively coupled to the display system, wherein the control system is configured to:

display a virtual object representing a tissue control point over the image of tissue in the user interface, wherein the virtual object is offset from a position of a first instrument;

operate a second instrument to move a proxy geometry representing the second instrument into contact with the virtual object and impart a force on the virtual object;

operate the first instrument based on the force applied to the virtual object to thereby manipulate the tissue; and generate a haptic feedback response at the second instrument in response to operation of the first instrument.

18. The apparatus of claim 17, further comprising:

an input device, wherein an input received through the input device operates the second instrument to move the proxy geometry representing the second instrument.

19. The apparatus of claim 18, wherein the input device comprises at least one of a touchscreen, a gesture tracking system, a gaze tracking system, a hand control device, a teleoperated device, or a mouse.

20. The apparatus of claim 18, wherein the haptic feedback response is applied to the input device.

* * * * *